United States Patent [19]

Senda et al.

[11] Patent Number: 5,756,907

[45] Date of Patent: May 26, 1998

[54] METHOD OF MEASURING PROPERTIES OF SAND

[75] Inventors: Yoshizumi Senda, Toyata; Tadashi Nishida, Toyokawa, both of Japan

[73] Assignee: Sintokogio, Ltd., Nagoya, Japan

[21] Appl. No.: 714,652

[22] Filed: Sep. 16, 1996

[30] Foreign Application Priority Data

Sep. 20, 1995 [JP] Japan .................. 7-241715

[51] Int. Cl.⁶ ............................................. G01N 33/00
[52] U.S. Cl. ......................... 73/866; 73/823; 73/38; 73/73
[58] Field of Search ....................... 73/823, 822, 866, 73/38, 821, 73, 818; 436/5

[56] References Cited

U.S. PATENT DOCUMENTS

| 3,638,478 | 2/1972 | Dietert et al. | 73/823 |
| 4,616,508 | 10/1986 | Jörn | 73/823 |
| 4,699,011 | 10/1987 | Bradway et al. | 73/823 |
| 4,930,354 | 6/1990 | Knopp et al. | 73/823 |

FOREIGN PATENT DOCUMENTS

| 6-40839 | 5/1994 | Japan | G01N 3/00 |
| 6-61346 | 8/1994 | Japan | B22C 5/00 |

*Primary Examiner*—Hezron E. Williams
*Assistant Examiner*—Nashmiya Ashraf
*Attorney, Agent, or Firm*—Limbach & Limbach L.L.P

[57] ABSTRACT

A method is provided for accurately and easily measuring properties of sand. This method includes the steps of measuring contraction properties of the sand, determining a molding parameter for molding a test piece of the sand having a known size based on the measurements of the contraction properties before the test piece is press-molded, press-molding the test piece by compacting a feed of the sand in accordance with the molding parameter, and measuring the properties of the sand by measuring properties of the test piece.

2 Claims, 3 Drawing Sheets

METHOD OF MEASURING PROPERTIES OF SAND

TECHNICAL FIELD

This invention relates to a method of measuring the properties of sand. More particularly, the invention relates to a method of measuring, for example, the strength, degree of ventilation, and deformation of casting sand used for a sand mold.

BACKGROUND

Green sand, which is the main type of casting sand used for a green sand mold, is produced by kneading a mixture with a mill or the like, which mixture consists of heat-resisting silica sand, bentonite as a caking agent, and water, coal powder, or starch, as an additive. Green sand once used for a green-sand mold is reused for forming a green-sand mold after it is collected and reclaimed. The used green sand is reused to form a green-sand mold after it is kneaded by again adding caking agents and additives thereto. This is because the used sand cannot be reused when left as is, as it has been affected by the heat of the molten metal, and as various caking agents added to improve the molding properties have changed upon reaction when they set.

The purpose of a mold is to set a cast metal by giving it a given shape or size to produce a given cast. Thus, casting sand used for a sand mold needs properties such as a good moldability, proper strength, hardness, or a degree of ventilation. However, the properties of the above-mentioned reclaimed sand have already changed due to the weight and shape of a cast to be molded. Thus, the reclaimed sand needs to be sampled and its strength and degree of ventilation need to be measured, to certify that its properties as casting sand are satisfactory.

Japanese Utility Model Early-Publication No. 6-61346 shows an apparatus for automatically measuring the water content, degree of ventilation, compactibility, and strength, of casting sand. In the apparatus casting sand is fed into a molding cylinder 90 for molding a test piece of a certain capacity (FIG. 3 of the present application), and then the upper end of the molding cylinder 90 is sealed while extra sand projecting from the upper end of the molding cylinder 90 is scraped away by a scraper 91. The sand is then compacted by raising an air-pressure cylinder 92 of a certain pressure from under the molding cylinder 90 so as to produce a test piece 93 (FIG. 4 of the present application). At this time, the compactibility is calculated by detecting the distance of the displacement A of the cylinder 92 by a magnetic displacement sensor 94. Then, the water content, degree of ventilation, and compressive strength, of the obtained test piece 93, are measured. The water content is calculated by detecting a change in the value of the electric resistance obtained by having the needle of a water sensor 95 penetrate the test piece 93. The degree of ventilation is calculated by ventilating the test piece 93 by sending air of a certain pressure from the air-pressure cylinder 92 via a vent hole 96, and by detecting the degree of depressurization by an air-pressure sensor 97. The compressive strength is calculated by having the air-pressure cylinder 92 press the test piece 93 against a load cell 98 so as to destroy it, and by detecting a load at the time of that destruction by the load cell 98.

However, the above conventional method has drawbacks in that since test pieces are produced by compacting casting sand filled in the test-piece molding cylinder 90 of a certain capacity by using the air-pressure cylinder 92 of a certain pressure, the height of each test piece 93 differs in accord with the kind and condition of sand, so that the measurements of the compressive strength or degree of ventilation also differ accordingly.

Japanese Utility Model Early-Publication No. 6-40839 shows a method of cutting a test piece into a piece of a certain height. However, there are difficulties in obtaining accurate measurements since the method causes the condition of the test piece to change by damaging it when it is cut.

This invention has been devised considering these circumstances. The technical theme to be dealt with by this invention is to provide a method that can easily and accurately measure the properties of sand even when the kind or condition of the sand differs.

DISCLOSURE OF INVENTION

The method of this invention of measuring the properties of sand to deal with the above theme is characterized by the steps of measuring the contraction properties of the sand, determining a feed of the sand based on the measurements of the contraction properties before a test piece of a given shape is press-molded, press-molding the test piece by compacting the feed of the sand, and measuring the properties of the sand by means of the test piece.

Although the contraction properties of sand can be represented, for example, by the measurement of its compactibility, the way of representing the sand properties is not limited thereto. The measurement of compactibility is generally represented by a percentage wherein casting sand is made to naturally fall into and fill a given container, and then the contraction ratio of the sampled sand is indicated by a percentage when a certain forced load is applied thereto. The measurement of the compactibility is used as a measurement of the properties indicating the moldability of the green sand.

In the method of this invention, the contraction properties of sand are first measured, the height (feed) of the sand to be fed is then adjusted before a test piece is press-molded based on the measurement, and then the test piece is press-molded by compacting the fed sand. Thus, test pieces of a certain height can be obtained even when the kind or condition of the sand differs so that the properties of the sand can be measured without being affected by the different heights of test pieces.

BRIEF DESCRIPTION OF THE DRAWINGS

FIGS. 1a–1g show a model process of the embodiment of this invention, wherein FIG. 1a shows a state in which sand has been fed, FIG. 1b shows a state in which extra sand has been removed, FIG. 1c shows a state in which the sand is pressurized to find the value of CB, FIG. 1d shows a state in which the height of the sand to be fed has been adjusted based on the CB value, FIG. 1e shows a state in which sand has been fed, FIG. 1f shows a state in which extra sand has been removed, and FIG. 1g shows a state in which a test piece with a height of H has been molded.

THE PREFERRED EMBODIMENT

An outline of the embodiment of this invention will now be explained by reference to FIGS. 1a–1g, showing a model process. As in FIG. 1a, a measuring mold 1 has a hole 1a whose section is a circle, in which hole 1a a lower pressure mold 2 is slidably positioned. The lower pressure mold 2 is moved up and down by driving means such as an air cylinder (not shown).

Figure 1A:
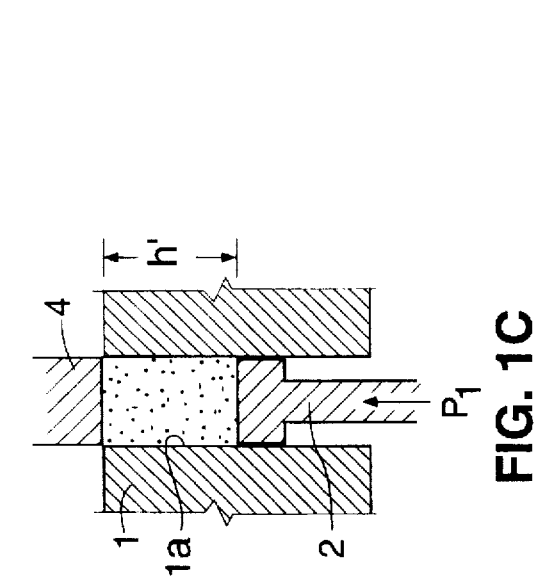

Sand is fed into the hole 1a, while the lower pressure mold 2 is arranged to provide a given depth of the hole 1a, namely, the height h of the sand before it is compressed, to be formed above the lower pressure mold 2 (FIG. 1a).

Figure 1B:
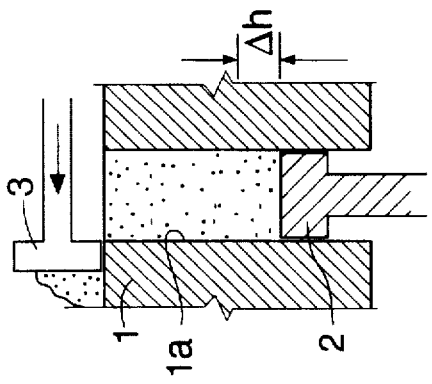
Figure 1C:
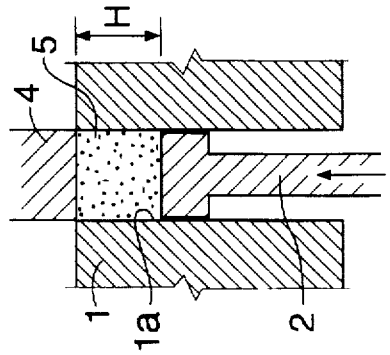

Next, as in FIG. 1b, extra sand at the upper end of the hole 1a is removed by using a jig 3, and then, as in FIG. 1c, the sand is compressed by moving the lower pressure mold 2 up with a constant pressure P1 being applied by the work of the air-pressure cylinder after the upper end of the hole 1a is closed by an upper pressure mold 4.

Then, the difference $\Delta h (\Delta h=h-h')$ between the height h of the sand before it is compressed and the h' of the sand after it is compressed is found, and, further, the compactibility (CB) is calculated by the following equation:

$$CB=(\Delta h/h) \times 100\% \quad (1)$$

Then, a height $\underline{a}$ of the sand to be fed to obtain a test piece of a predetermined height H is calculated by the following equation:

$$a=H/\{(100-CB)/100\} \quad (2)$$

Figure 1D:
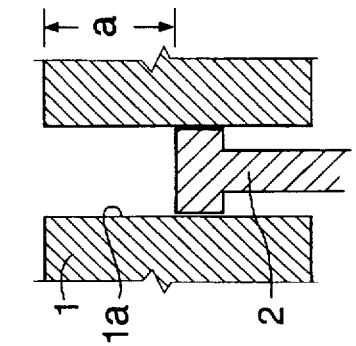
Figure 1E:
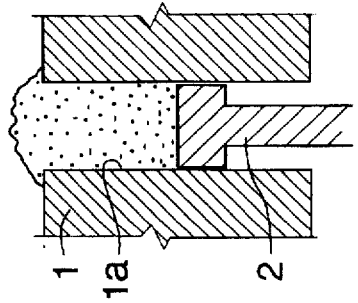

Next, as in FIG. 1d, the lower pressure mold 2 is disposed such that the depth of the hole 1a formed above the mold 2 becomes $\underline{a}$ in accord with the calculated height $\underline{a}$, and then, as in FIG. 1e, the sand is fed into the hole 1a.

Figure 1F:
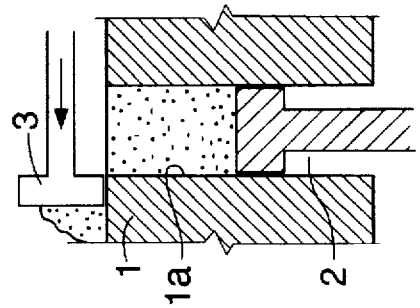
Figure 1G:
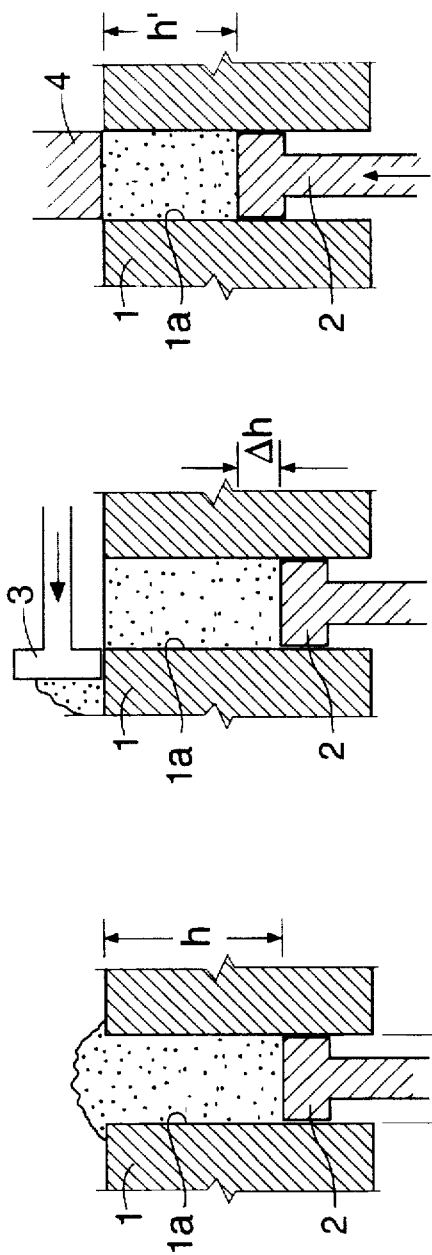

Next, as in FIG. 1f, extra sand at the upper end of the hole 1a is removed by using a jig 3, and then, as in FIG. 1f, the sand is compressed by moving the lower pressure mold 2 up with a constant pressure P1 being applied by the work of the air-pressure cylinder after the upper end of the hole 1a is covered with an upper pressure mold 4, thereby always allowing a test piece 5 of a certain height H to be obtained.

The test piece 5 thus obtained is then used to measure the compressive strength, degree of ventilation, or water content, of the sand. Thus, as a test piece 5 of a certain height H is obtained in accord with the embodiment, regardless of the kind or condition of sand, the properties of the sand such as the degree of ventilation, compressive strength, or water content, can be determined without being affected by the height of the test pieces.

The preferred embodiment will now be specifically explained as follows:

Sand sample Nos. 1–5 were prepared by mixing silica sand as a main component with bentonite as a caking agent and water and coal powder as additives, and by kneading the mixture for a given time with a mill. The distribution ratios of the coal powder and bentonite were set at 4 wt. % and 7 wt. % respectively, and the distribution ratios of the silica sand and water were changed so as to be adapted to sample Nos. 1–5.

Test piece Nos. 1–5 of a certain height H were produced for all of sample Nos. 1–5 in accord with the above-mentioned method. In this embodiment the diameter of the hole 1a of the measuring mold 1 was 50 mm, the height of the same before it was compressed was 100 mm, and the pressure P1 applied to the lower pressure mold 2 was 2 MPa, both when compactibility was measured and when the test pieces were press-formed.

Table 1 lists values for compactibility (CB), calculated from the heights of sand h' after the sand is compressed and the differences $\Delta h(\Delta h=h-h')$, for all sample Nos. 1–5, by using above equation (1), the heights $\underline{a}$ of sand to be fed, calculated from the values of CB by using above equation (2), and the heights H of test pieces after they are press-molded.

TABLE 1

| Samp. Nos. | CB (%) | $\underline{a}$ (mm) | H (mm) |
|---|---|---|---|
| 1 | 22 | 64.1 | 49.99 |
| 2 | 26 | 67.6 | 50.05 |
| 3 | 37 | 79.4 | 50.00 |
| 4 | 48 | 96.2 | 49.98 |
| 5 | 52 | 104.2 | 50.01 |

As is clear from Table 1, heights H of 50±1 mm for test pieces are achieved by adjusting the height $\underline{a}$ of the sand to be fed based on the values of CB.

The height H of the test pieces was set at 50 mm for these reasons: As in FIG. 2, the relationships between the heights H of the test pieces and their compressive strengths reveal that the lower the height H of the test pieces, the more remarkable are the variations of the values of the compressive strength, and the values of the compressive strength become constant when the height H is over 50 mm. Further, it is generally well known that when the height H of test pieces is too high, uniform test pieces cannot be obtained since the difference in the density at each end of the test piece becomes great, namely, between the one end at which a pressure is applied, and the other end where no pressure is applied. Thus, a uniform test piece has been obtained by adopting a height of 50 mm, at which height its compressive strength becomes substantially constant.

Figure 2:
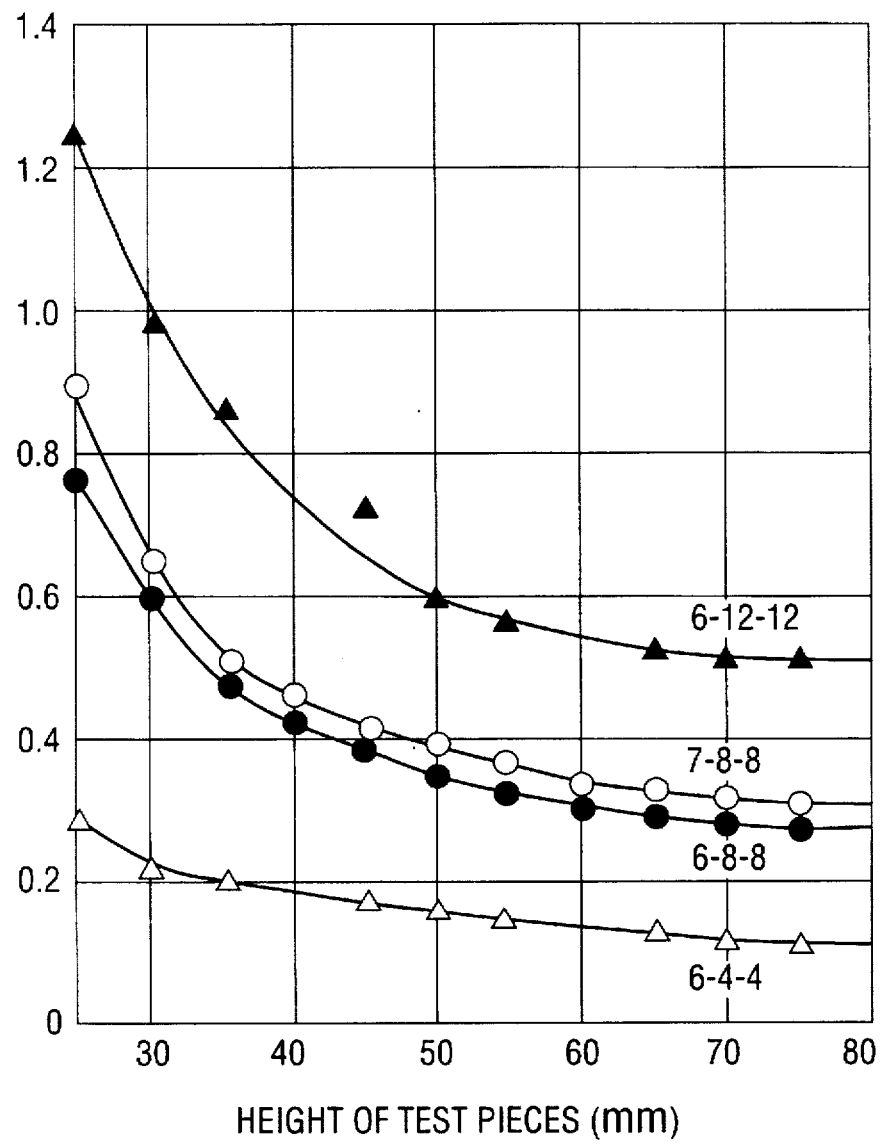
FIG. 2 is a graph showing a relationship between the heights H of test pieces and the values of compressive strength.
Figure 3:
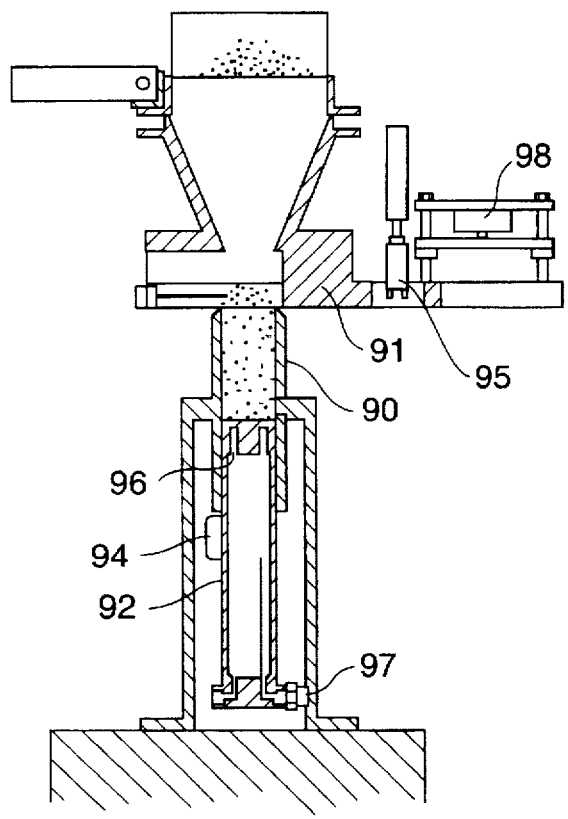
FIG. 3 is a section showing a state in which sand has been fed into a cylinder for press-molding a test piece in accord with a conventional method.
Figure 4:
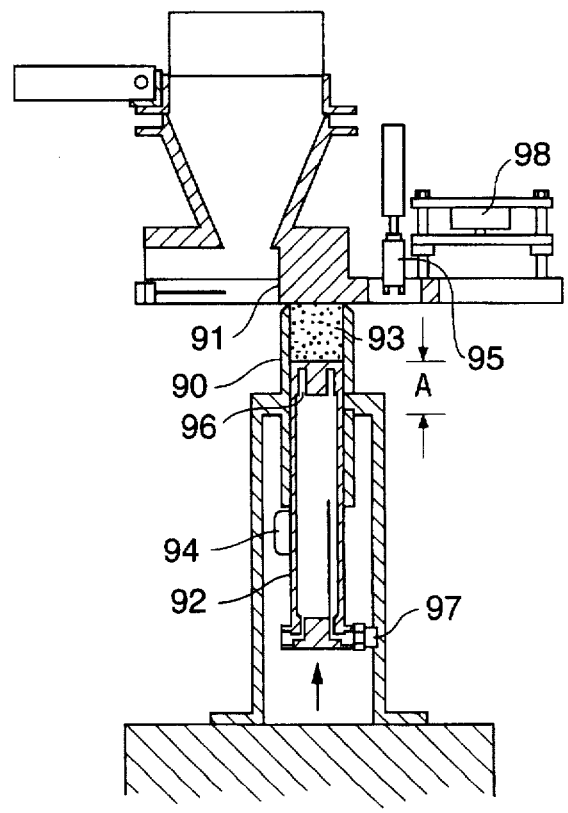
FIG. 4 is a section showing a state in which a test piece has been press-molded in accord with a conventional method.

In FIG. 2, the line indicated by "6-12-12" denotes a mixture of No. 6 silica sand, 12 wt. % of bentonite, and 12 wt. % of water. The line indicated by "7-8-8" denotes a mixture of No. 7 silica sand, 8 wt. % of bentonite, and 8 wt. % of water. The line indicated by "6-8-8" denotes a mixture of No. 6 silica sand, 8 wt. % of bentonite, and 8 wt. % of water. The line indicated by "6-4-4" denotes a mixture of No. 6 silica sand, 4 wt. % of bentonite, and 4 wt. % of water.

As detailed above, by using the method of this invention for measuring the properties of sand, a test piece with a predetermined height can be obtained even when the kind or condition of the sand differs, so that the properties of sand can be accurately and easily determined without being affected by the height of test pieces. Thus, by using the method of this invention when, for example, the properties of casting sand or sand reclaimed therefrom are measured, one can provide casting sand or sand reclaimed therefrom whose properties are stable.

What is claimed is:

1. A method of measuring properties of sand, comprising the steps of:

press molding a sample of sand, measuring contraction properties of the sand from said press molding step, determining a molding parameter for molding a test piece of the sand having a predetermined size parameter based on the measurements of the contraction properties before the test piece is press-molded, press-molding the test piece by compacting a feed of the sand in accordance with the molding parameter so as to obtain the test piece having said predetermined size parameter, and measuring the properties of the sand by measuring properties of the test piece.

2. The method of claim 1, wherein the predetermined size parameter is a predetermined height.

* * * * *